Nov. 9, 1954
R. G. JELLY
ROSE PLANT
Filed Oct. 26, 1953
Plant Pat. 1,315
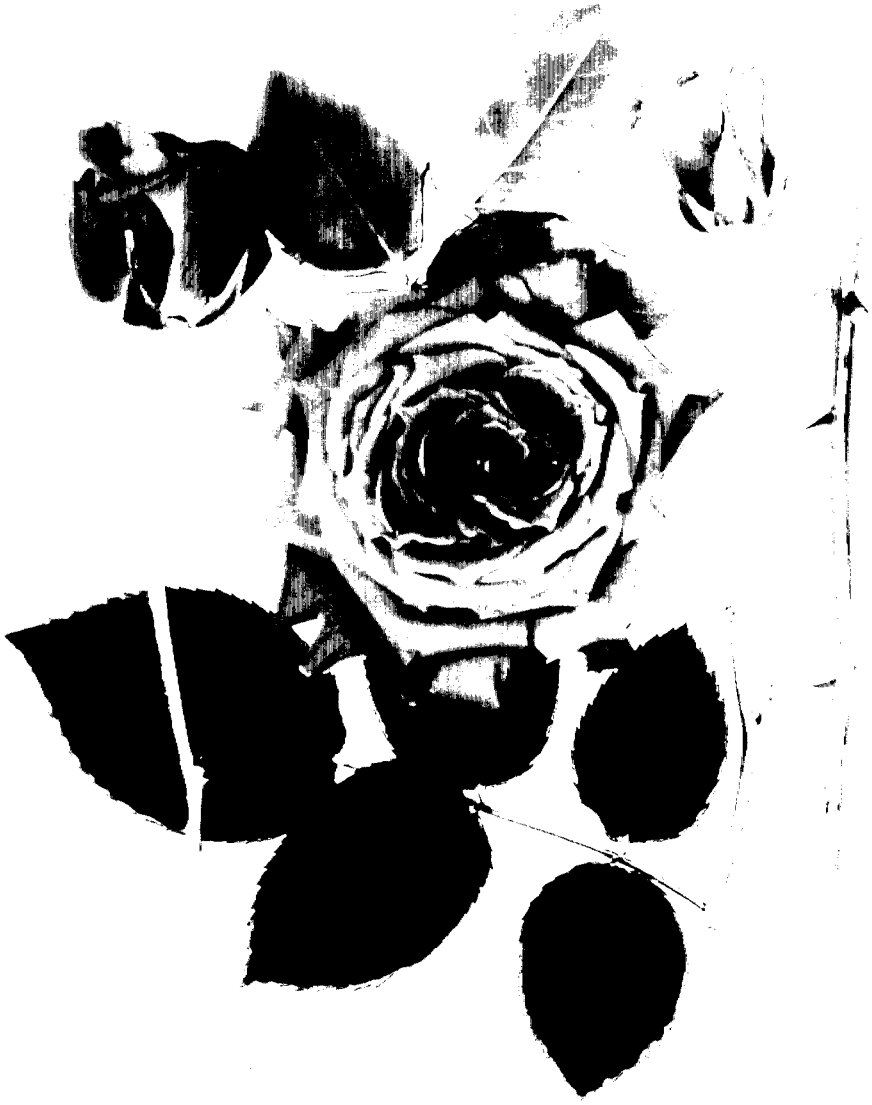
Inventor.
R. G. Jelly
By: Cobb & Cobb
Attorneys.

United States Patent Office

Plant Pat. 1,315

Patented Nov. 9, 1954

1,315

ROSE PLANT

Robert G. Jelly, Richmond, Ind., assignor to E. G. Hill Co., Inc., Richmond, Ind., a corporation of Indiana Application October 26, 1953, Serial No. 388,467

1 Claim. (Cl. 47—61)

The present invention relates to a new and distinct variety of rose plant of the hybrid polyantha class which was originated by me by crossing the variety "Garnette" (unpatented) with an unnamed and unpatented seedling of unknown origin.

The primary objective in making this cross was to produce a new polyantha type rose which would not cluster too freely, yet which would produce blooms of long-keeping quality when used commercially for cut-flower production. This objective was fully achieved, and in addition, my new variety is characterized by a freer and more upright growth, and produces larger buds than the variety "Garnette." The buds, moreover, are quite distinctive and attractive in color, and are especially clean and free, while the flowers are endowed with excellent keeping qualities when cut from the bush, and while on the bush, they make a very good showing against the attractive foliage.

Another outstanding characteristic of my new variety is that it responds exceedingly well to "pinching," which involves discarding a bloom before maturity in order to produce a bloom of better quality at a more favorable time, as commonly practiced by florists engaged in cut-flower production.

The foregoing characteristics definitely distinguish my new variety from its parents, as well as from all other varieties of its class, and present a unique combination of features in a rose of this type.

Asexual reproduction of my new variety by grafting at Richmond, Indiana, shows that the foregoing characteristics come true to form and are established and transmitted through succeeding propagations.

The accompanying drawing shows typical specimens of the flowers, foliage and stems of my new variety in different stages of development and depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson"), Koster's Color Guide (hereinafter abbreviated as "Koster") and Ridgway's Color Standards and Nomenclature (hereinafter abbreviated as "Ridgway"):

Type: Seedling; greenhouse; for cut-flower production.
Class: Polyantha (usually disbudded commercially to sell as solitary flowers).
Breeding: Seedling.
*Seed parent.*—"Garnette."
*Pollen parent.*—An unnamed seedling of unknown origin.
Propagation: Holds its distinguishing characteristics through succeeding propagations by grafting.

*Flower*

Locality where grown and observed: Richmond, Indiana.
Flowers borne: From 1 to 3 to stem; on moderately strong stems of medium length.
Quantity of bloom: Abundant, in greenhouse.
Continuity: Continuous.
Fragrance: Slight; sweetbriar.
Bud:
*Peduncle.*—Medium length; small diameter; strong; erect; smooth; no thorns, prickles or hairs. Color—Fern Green, Plate o862/1 (Wilson).
*Before calyx breaks.*—Size—small. Form—Short-pointed; ovoid; with a conspicuous neck; with slender foliaceous appendages on the surface of the bud; with foliaceous parts extending beyond the tip of the bud equal to ¼ or more of its length. Color—Scheele's Green, Plate 860/2 (Wilson).
*As calyx breaks.*—Color—Chrysanthemum Crimson, Plate 824/1 (Wilson).
*As first petal opens.*—Size—medium-small. Form—Long-pointed. Color—outside—Crimson, Plate 22/1 (Wilson); inside—Indian Lake, Plate 826 (Wilson).
*Opening.*—Opens up well in greenhouse; is not affected by hot or dry weather.
Bloom:
*Size (when fully open).*—Small; from 2½ to 4 inches.
*Petalage.*—Double; from 45 to 55 petals; arranged regularly.
*Form.*—High-centered at first; but becoming very cupped and high-centered; petals being at first rolled inward, but becoming rolled outward later at maturity.
Petals: Moderately thick; with inside velvety and outside satiny.
*Shape.*—Outside—ovate; apex mucronate, with 1 or more notches. Intermediate—obovate; apex cuspidate. Inside ovate to obovate; apex cuspidate.

This description of a newly opened flower was made from a rose grown in a greenhouse in the month of February at Richmond, Indiana:

*Color*—Outside petal; outside surface—Rose Red, Plate 724/3 (Wilson); inside surface—Rose Red, Plate 724 (Wilson), with a Dresden Yellow, Plate 64/3 (Wilson) base. Intermediate petal: outside surface—China Rose, Plate o24/1 (Wilson); inside surface—Rose Red, Plate 724 (Wilson). Inner petal: outside surface—Rose Red, Plate 724/2 (Wilson); inside surface—a tint slightly deeper than Rose Red, Plate 724 (Wilson), with a velvety texture (no exact comparative shade found in color charts).

This description was made from a rose that was open for three days in a greenhouse in the month of February at Richmond, Indiana:

*Color.*—Outside petal: outside surface—Rose Red, Plate 724/2 (Wilson); inside surface—Rose Red, Plate 724 (Wilson). Intermediate petal: outside surface—Rose Red, Plate 724/3 (Wilson); inside surface—Rose Red, Plate 724 (Wilson). Inner petal: outside surface—Rose Red, Plate 724/3 (Wilson); inside surface—Rose Red, Plate 724 (Wilson).
*General color effect.*—Newly opened flower—Rose Red, Plate 724 (Wilson). 3-days open—Rose Red, Plate 724/1 (Wilson).
*Behavior (in greenhouse).*—Persist; unaffected by hot or dry weather; starts to fade after 6 days open on plant, fading to China Rose, Plate o24/1 Wilson).
*Flower longevity.*—Cut flowers grown in greenhouse and kept at living-room temperatures—7 days in February.

*Plant*

Foliage:
*Leaves.*—Usually compound of 7 leaflets, but sometimes 5 or 3 leaflets; normal; medium size; moderately leathery.
*Leaflets.*—Shape—ovoid. Apex—acute. Base—round to acute. Margin—serrate. Color—mature: upper surface—Parsley Green, Plate oo962 (Wilson); under surface—Lavender Green, Plate ooo761/1 (Wilson). Young: upper surface—Maroon, Plate 1030 (Wilson); under surface—Maroon, Plate 1030/1 (Wilson). Rachis—light to medium. Upper side—grooved; slightly prickly. Under side—almost smooth. Stipules—short; narrow; with points of medium length turning out at an angle of less than 90° and recurved slightly toward stem.

Growth (in greenhouse):

*Habit.*—Upright; much-branched.

*Growth.*—Free; vigorous.

*Canes.*—Small to medium diameter.

*Main stems.*—Color—Spinach Green, Plate o960/3 (Wilson). Thorns—several; short; hooked slightly downward; with narrow base. Color—Tobacco Brown, Plate 88 (Koster). Prickles—none. Hairs—none.

*Branches.*—Color—Spinach Green, Plate o960/2 (Wilson). Thorns — several; medium length; hooked very slightly downward; with broad base. Color — Oil Yellow, Plate V (Ridgway). Prickles—none. Hairs—none.

*New shoots.*—Color—Spinach Green, Plate o960/2 (Wilson). Thorns — several; medium length; hooked downward; with narrow base. Color—Currant Red, Plate 821 (Wilson). Prickles—none. Hairs—none.

*Reproductive organs*

Stamens: Medium number; arranged regularly about pistils; tucked in calyx.

Filaments: Short; many; most with anthers. Color—Naples Yellow, Plate 403/1 (Wilson).

Anthers: Medium; all open at once. Color—Yellow Ochre, Plate o7 (Wilson).

Pollen: Moderate. Color—Apricot Yellow, Plate IV (Ridgway).

Pistils: Medium number.

Styles: Uneven; medium length; moderately thin; bunched; columnar. Color—Martius Yellow, Plate IV (Ridgway).

Stigma: Color—Cherry, Plate 722/1 (Wilson).

Ovaries: Some protruding from calyx.

Hips: Short, flat top; pointed base; with conspicuous neck; gourd-shaped; very smooth; walls thin and fleshy. Color—Persimmon Orange, Plate 7/0 (Wilson).

Sepals: Permanent; medium length; spear-shaped; recurved.

*Color.*—Inside—Lavender Green, Plate ooo761 (Wilson). Outside—Willow Green, Plate ooo862 (Wilson).

Seeds: Few; small to medium size.

I claim:

A new and distinct variety of rose plant of the hybrid polyantha class, substantially as herein shown and described, characterized particularly as to novelty by its vigorous, free and upright habit of growth, by its clean, free and relatively large buds of distinctive color, by its attractive foliage, by the excellent keeping quality of its flowers when cut from the bush, and by its excellent response to "pinching" for commercial production of cut-flowers in greenhouses.

No references cited.